United States Patent [19]

Lahmani et al.

[11] Patent Number: 5,455,048
[45] Date of Patent: Oct. 3, 1995

[54] SUN FILTER MICROCAPSULES

[75] Inventors: Paul Lahmani, Tours; Lise Simoneau-Agopian, Marseille, both of France

[73] Assignee: Roussel UCLAF, Paris, France

[21] Appl. No.: 869,734

[22] Filed: Apr. 16, 1992

[30] Foreign Application Priority Data

Apr. 19, 1991 [FR] France .................................... 91 04881

[51] Int. Cl.$^6$ ...................................... A61K 9/16
[52] U.S. Cl. ........................ 424/490; 424/489; 424/456
[58] Field of Search .................................. 424/490, 489, 424/456, 59

[56] References Cited

U.S. PATENT DOCUMENTS

| | | | |
|---|---|---|---|
| 3,872,024 | 3/1975 | Hurger | 252/316 |
| 4,107,288 | 8/1978 | Oppenheim et al. | 424/499 |
| 4,731,242 | 3/1988 | Palinczar | 424/59 |
| 5,071,706 | 12/1991 | Soper | 424/489 |
| 5,089,269 | 2/1992 | Noda | 424/456 |

OTHER PUBLICATIONS

Copy of Search Report (3 pages).

*Primary Examiner*—Thurman K. Page
*Assistant Examiner*—William E. Benston
*Attorney, Agent, or Firm*—Bierman and Muserlian

[57] ABSTRACT

Microcapsules containing at least one sun filter having been hardened so as to be impervious with a size of 1 to 1250 micrometers whereby the sun filters do not come in contact with the skin.

13 Claims, No Drawings

SUN FILTER MICROCAPSULES

STATE OF THE ART

For a long time the cosmetic industry has made available to people, products such as gels, creams, oils incorporating sun filters which are chemical substances which absorb UVA and/or UVB rays. It is useful to limit the effects of solar rays at the skin level, particularly those of UVB and UVA. The first cause sun erythema and in the longer term benign and malignant skin changes and the second rays are the main factor in skin ageing.

Sun protection products are very useful because they actually provide a protection for the skin which is measured by what is called a protection factor. However, their presence on the skin, although it is very beneficial due to the protection against UVA and UVB rays, is not completely harmless. To such a degree that most regulatory bodies have put together positive lists of sun filters which means that cosmetic products can contain only filters registered on this list and which have been proven to be fairly harmless. This is the case in France and in the EEC. In the USA, products containing sun filters are considered as quasi-medicaments and are part of a separate category; O.T.C. (Over The Counter) products.

It therefore appeared sensible to find a means of putting sun filters on the skin without them being in direct contact with it. One of the methods used is encapsulation or microencapsulation as described in U.S. Pat. No. 4,904,524 and EP Pat. No. 0,254,447. However, the microcapsules described in the prior art which contain sunfilters as in U.S. Pat. No. 4,904,524 are not impervious.

OBJECTS OF THE INVENTION

It is an object of the invention to provide microcapsules containing sun filters which have been hardened so they will not be crushed during use, are non-porous so the sun filters will not leak out and resistant to softening when in contact with other components of a cosmetic composition and a process for their preparation.

It is another object of the invention to provide cosmetic compositions containing said microcapsules and a cosmetic method.

These and other objects and advantages of the invention will become obvious from the following detailed description.

THE INVENTION

The novel microcapsules of the invention containing at least one sun filter have been hardened so as to be impervious whereby the sun filter(s) do not leak out during manufacture, storage or application to the skin. In a preferred embodiment, the wall of the microcapsules contain gelatin which has been hardened with a hardening agent, preferably glutaraldehyde.

The size of the microcapsules must be small so the microcapsules are not felt when applied to the skin and to ensure a homogenous presence of the sun filter on the top of the skin. The desired size is 1 to 1250 microns, preferably 20 to 200 microns. The range is more preferably 30 to 80 and most preferably 40 to 45 microns.

Examples of sun filters which may be used in pure form or diluted with an oil are octyl methoxycinnamate, ethyl hexyl 4-methoxycinnamate, camphor methylbenzylidene, isoamyl methoxycinnamate, octyldimethyl PABA, PABA or 4-amino benzoic acid, homosalate, octyl salicylate, butyl methoxydibenzoyl-methane, isopropyl dibenzoylmethane, oxybenzone, octyl triazone. This list is exemplary only and any sun filter or any liposoluble chemical substance with a filtering effect may be used.

The microcapsules can contain an oily phase consisting of 50 to 100% sun filters and any oil commonly used in cosmetology such as vaseline oil, perhydrosqualen, polyisobutene, dioctylcyclohexane, sunflower oil, castor oil, evening primrose oil, olive oil, jojoba oil, muscat rosebush oil, sesame oil, propylene glycol dioctonoate, propylene glycol dicaprate/dicaprylate, isocetyl isostearate, polydimethyl cyclosiloxane, octyl dodecanol, polyphenyl methyhlsiloxane or lanoline oil.

The Pharmacopoeia gives the following definition of microencapsulation: "Microcapsules are solid products composed of an envelope itself solid containing a liquid, a solid or a pasty substance. They are obtained by various processes, such as coacervation, interfacial polymerization".

The different processes of microencapsulation provide microparticles of very varied structure and morphology. A simple classification aims to group these different structures into two categories: A) microspheres or matrix systems which are full spherical particles in which the active ingredient to be encapsulated is homogeneously dispersed in the support material (continuous network of support material) and B) microcapsules or reservoir system which are hollow spherical particles, the active ingredient being inside in a solid, liquid or pasty state surrounded by a solid membrane devoid of active ingredient. It is this category which is used in the present invention. Examples of microcapsule preparations are also described in the European Pat. No. 0,025,379 and No. 0,399,911.

The process of the invention is a complex coacervation process and comprises forming a dispersion of the sun filter in a colloidal solution, subjecting the dispersion to coacervation and formation of a ternary system by pH variation, encapsulating the dispersed sun filter, hardening the walls of the microcapsules and recovery of the microcapsules. The pH is between 3 and 7, preferably 4 to 5.

The term coacervation (from the Latin acervus) means aggregation and describes the phenomenon of desolvation of macromolecules (aggregation of macromolecules between themselves) leading to a phase separation in initially homogeneous and diluted solutions. Indeed, a macromolecular substance in the presence of a solvent gives a colloidal solution (the molecules of water are fixed by the macromolecules).

Under the effect of the variation of a physico-chemical parameter, namely the pH, the attraction forces between the molecules are stronger than those which connect them to the solvent (there is therefore desolvation), and a new phase appears—the coacervate, constituted by distinct droplets rich in macromolecular substances which will envelope the particles like a capsule.

The complex coacervation results from the interaction of two polymers of opposing electrical charge of which at least one must be a colloid such as gelatin and gum arabic, gelatin and sodium alginate, gelatin and sodium polyphosphate. This interaction between the two polymers can result in a complex whose solubility is reduced to a such a point that a phase separation occurs, separation into two phases one of which is low in polymers and rich in solvent, and the other rich in polymers (P+/P−).

The gelatin is a macroprotein and the complex coacervation brings into play ionized groups of gelatin. For example, at a pH lower than the isoelectric point, the gelatin is positively charged. Thus, by adjusting the pH of the medium because the charges on the chain vary as a function of the pH where the two polymers are found, the positive charges on the gelatin (lysine unit) can be exactly neutralized by the negative charges on the second polymer (gum arabic, sodium polyphosphate which is an inorganic polymer).

In a preferred mode of the process, the complex coacervation can be carried out in four phases: 1) preparation of the colloidal solution or dispersion of the substance to be encapsulated in this solution, 2) phase separation (or coacervation) and formation of a ternary system by variation of the pH, 3) encapsulation of the dispersed substance, and 4) hardening of the wall and separation of the microcapsules to obtain solid particles.

The first polymer is preferably gelatin which is constituted by amino acids. The bond between the monomers is brought about by peptidic bonding and the fine structure of the gelatin can be defined as a sequence of $(glycine-X-Y)_n$ type, the amino acids often being, respectively, proline and hydroxyproline.

The second polymer is sodium polyphosphate, preferably sodium hexametaphosphate. The hardening agent is preferably glutaraldehyde in solution at 25% in water and the oil phase is a sun filter, for example ethyl hexyl 4- methoxycinnamate or octyl methoxycinnamate (PARSOL MCX®).

The process of the invention may be modified by the addition of surfactants, the speed of stirring, the shape of the stirrer blades, etc. The most useful variation of the process consists of the addition during the formation of the initial emulsion of nonionic surfactants at a rate of 1 to 5% by weight of the mixture.

Also the speed of stirring can be between 300 and 1500 rpm and preferably 800 to 1000 rpm.

As a function of the conditions, the yield of the microencapsulation as well as the size of the microcapsules will be variable, i.e. microcapsules whose size varies between 30 microns and 150 microns.

The process modified by the addition of nonionic surfactants allows a size population of from 30 to 80 microns to be obtained with a homogeneous maximum between 40 and 45 microns. The surfactant can be chosen, for example, from the following non-exhaustive list: MONTANE 20, MONTANE 80, (Sorbitan Monolaurate POE), Sodium lauryl sulfate, TWEEN 20, TWEEN 80, (Polysorbate 20 or 80), DEHYTON K, (cocomidoprony-betaine). Preferably, the surfactant used will be non-ionic and is MONTANE 20 (Sorbitan monolaurate POE). The amount of surfactant used can be 0.5% to 5% of the preparation and preferably 1%.

The antisun cosmetic compositions of the invention are comprised of an anti solar effective amount of the microcapsules of the invention incorporated into a cosmetic composition or base to protect the skin from ultraviolet A and B rays. The compositions ensure that there is no contact between the sunfilters and the skin while retaining the ability to act as physical reflections of UVA and UVB rays.

The compositions may be in the form of aqueous gels, oily gels, plain or water-in-oil emulsions, plain or oil-in-water emulsions, multiple emulsions, water-in-oil-in-water or oil-in-water-in-oil, for example: a triple water-in-oil-in-water emulsion, a triple oil-in-water-in oil emulsion, an oil-in-water emulsion containing liquid crystals, complex emulsions containing liquid crystals forming lipid bilayers surrounding the oily phases, pseudo-emulsions (dispersion of an oily phase, or water-in-oil emulsion in a gelified aqueous phase without traditional surfactants, oil in-water or water-in-oil micro-emulsions, emulsions containing two dispersed oil phases, different from and insoluble in each other, a pseudo-emulsion or dispersion of an oily phase dispersed in an aqueous phase and stabilized with Lubragel®, polyglycerol methacrylate propylene glycol of Pemulen®, alkyl acrylate trans polymer type polymers, Hypan®, xanthane gum, CMC ( 1-cyclohexyl-3-(2-morpholinoethyl) carbodiimide), hyroxyethyl cellulose, Amigel® type polyaccharides, polyvinylpyrrolidone, or a mixture of two or more of these gelling agents.

It is clear that the microcapsules containing sun filters and suitably hardened are insoluble in the various composition phases and therefore constitute an additional phase. The cosmetic compositions can contain at least 1 to 50% of of microcapsulses containing sun filters and microcapsules containing different sun filters can be added to the same composition.

Finally, sun reflectors can be added to these cosmetic compositions to strengthen the protective power. They are generally products insoluble in the aqueous and oily phases and therefore are an additional phase: They may be perfluoroethers such as FOMBLIN® from the Montecatini Company, insoluble pigments such as titanium oxide, rutile titanium oxide, anatase titanium oxide, pyrogeneous titanium oxide such as P 25® from Degussa, micronized titanium oxide in SUN VEIL® from Ikeda, titanium oxide surface treated by silicones or by amino acids, or by lecithin or by metallic stearates, iron oxide, iron oxide surface-treated by silicones, or by amino acids, or by lecithin, or by metallic stearates, zinc oxide, micronized zinc oxide such as UFZ0® from Cosmo Trends corporation and mica covered with titanium oxide.

The novel method of protecting the skin from the sun's rays comprising applying to the skin a solar protecting amount of a cosmetic composition containing the microcapsules of the invention. The method prevents and treats skin diseases caused by UVA and UVB rays. The compositions may also contain pharmaceuticals.

In the following examples, there are described several preferred embodiments to illustrate the invention. However, it should be understood that the invention is not intended to be limited to the specific embodiments.

EXAMPLE 1

Hard microcapsules containing PARSOL MXC® (octyl methoxycinnamate)

10 g of gelatin were placed in 120 ml of demineralized water at 80° C. and then, 90 ml of Parsol MCX® were dispersed in this solution. Coacervation was produced by the addition at about 55° C. of a solution of 1 g of sodium hexametaphosphate in 20 ml of distilled water and the mixture was diluted with 100 ml of distilled water. Then, the pH was lowered by the addition of glacial acetic acid until a pH of about 4.2 was reached. Then, the reaction medium was suddenly cooled to 5° C. and was maintained at this temperature for about 30 minutes. Hardening by cross-linking was carried out by addition of 5 ml of a 25% solution of glutaraldehyde and the mixture was allowed to react for 12 to 24 hours at ambient temperature. Then, the microcapsules were removed by filtration and dried in a fluidized air bed.

EXAMPLE 2

Hard microcapsules containing PARSOL MCX®

90 ml of PARSOL MCX® containing 0.5 to 5% polysorbate 20, a non-ionic surfactant intended to increase the yield of microcapsules and to obtain a more homogeneous microcapsule size, were dispersed in a solution of 10 g of gelatin in 120 ml of demineralized water at 80° C. to obtain a population of microcapsules whose size ranged from 30 to 80 microns with a maximum (more than 30%) between 40 and 45 microns.

EXAMPLE 3

An oil-in-water emulsion was prepared in the following manner: The components of the following oily phase were heated at 80° C.:

| | |
|---|---|
| self-emulsionable glycerol stearate (arlacel 165 ® from ICI Company) | 6 g |
| ketyl alcohol | 1 g |
| ethoxylated soya sterol (generol 122 E 10 ® from Henkel Company) | 2 g |
| mixture of vaseline oil and lanolin alcohol (amerchol L101 ® from Amerchol Company) | 3 g |
| petrolatum and lanoline alcohol (Amerchol CAB ® from Amerchol Company) | 1 g |
| safflower oil | 6 g |
| karite butter | 3 g |
| Propyl parabene | 0.05 g |

In addition, the following aqueous phase was prepared which was also heated to 80° C.:

| | |
|---|---|
| demineralized water | 60 g |
| sorbitol at 70% | 3 g |
| xanthane gum | 0.3 g |
| methyl parabene | 0.1 g |

When the xanthane gum was well dispersed, the oily phase was added to the aqueous phase at 80° C., and stirring was carried out vigorously for 20 minutes to form an emulsion. Then, the stirring was reduced and the emulsion was cooled slowly to 40° C. Then, 2 g of water containing 0.15 g of imidazolidinyl urea and then 0.3 g of perfume were added to the emulsion. At this temperature, 6.6 g of microcapsules prepared as indicated above in Example 1 or 2 of the invention were added to obtain capsules containing 80% pure Parsol MCX® relative to the weight of microcapsules or 5.28% pure Parsol MCX®.

EXAMPLE 4

The same preparation of Example 3 had added to it 9.9% of microcapsules which represented a 7.92% concentration of pure Parsol MCX®.

EXAMPLE 5 a) An oily gel was prepared with the formula:

| | |
|---|---|
| thick vaseline oil | QS 100 g |
| octyl stearate | 10.0 g |
| karite butter | 2.0 g |
| $C_{18}$–$C_{36}$ glycolic acid esters (synchrowax from CRODA Company) | 4.0 g |
| evening primrose oil | 1.0 g |
| safflower oil | 5.0 g |
| Propyl parabene | 0.1 g |

These products were heated until homogeneous and then 3 g of pyrogeneous silica (aerosil 200 from DEGUSSA Company) were added with good stirring. When the silica was well dispersed, the following were added: 3% of a solution of silymarine extract in polyethylene glycol 400; 0.2% of N-acetyl tyrosine and 0.3% of a perfume composition. Then, 10 g of microcapsules prepared as described above and containing pure Parsol MCX® were added for a content of Parsol MCX® of 76% of the total weight of microcapsules which means the composition contains 7.6% Parsol MCX®.

Test for determination of the sun protection factor UV Source:

The source of UV light was a 150 watt Xenon lamp, without ozone filtered with WG 320 of 1 mm. After flux adjustment with a diaphragm, the light was directed onto 6 liquid filled light guides which provided a cold light. The end of the guides was situated 1 millimeter from the skin of the back being tested and the guides were held together by a block allowing their simultaneous use.

Dosimetry:

A calibrated Robertson-Berger dosimeter, for the response of the human epidermis to solar UV, was used to calculate the doses supplied to each guide end. The doses were adjusted using diaphragms and increased by 1.25. The dosimetry expresses the doses in MED per minute and UVs were supplied for the same length of time for each guide.

Preliminary clinical examination:

Each volunteer had a physical examination of the test area, the back between the belt and the top of the scapulae to determine the possible presence of: solar erythema, residual pigmentation, scars, various epidermal and dermal lesions, and abnormalities of skin pigmentation.

Volunteers:

7 human volunteers in good health without photosensitivity anamnesis, not having been exposed to the sun for 3 months, were selected from all the volunteers. Each of them was informed of the aims, processes and potential risks of this test. An informed consent was obtained for each volunteer before the start of the test.

Assessment of the skin type of the patients:

Before exposures, each volunteer answered a written questionnaire consisting of 5 sections corresponding to different situations of sun sensitivity or capacity to acquire a tan. According to the replies, the patients were placed in one of the 6 categories representing the melanogenotypes of caucasian skins, and in 4 phototypes.

Preliminary determination of the Minimal Erythemal Dose:

To determine the UV sensitivity of the volunteers, a series of 6 UV exposures was applied to the treatment area and 24 hours before the test, each exposure was 1.25 times greater than the previous exposure. 24 hours after the radiation exposure, the radiated areas were examined and the minimal erythemal dose (MED) was recorded which MED was used as an indicator to fix the necessary exposure time for the main test.

Determination of the test area:

The outline of a 100 cm$^2$ template was traced on the back and an applied product corresponded to each area.

Use of the product being tested and the standard product:

The product tested was weighed in units of 2.2 g and the standard product was introduced into a syringe of insulin type without air bubbles. A quantity of 2 mg/cm$^2$, that being 0.2 ml, was applied over the test areas (100 cm$^2$) and the products were spread out with the finger very evenly by light massage for a few minutes.

Waiting time:

After use, there was a rest period of 15 minutes before irradiation.

Exposure of the test area:

The machine carrying the guides was applied to the test area, and the irradiation was continued for a time proportional to the theoretical MED and PF (protection factor) of the product. After irradiation, each volunteer was instructed not to expose himself to UV radiation and to come for examination after 24 hours.

Determination of the response:

24 hours ±2 hours after irradiation, the response of the treated skin was evaluated by the following criteria: absence of erythema, trace of erythema, incomplete or irregular erythema, regular well-defined erythema-MED, large erythema and mauvish erythema with oedema (minimal oedematous dose-3 MED).

Calculation of the sun protection factor:

The individual sun protection factor for each volunteer was the ratio of the MED values for treated and non-treated skin. The individual results (20) were added together, and the arithmetical average was calculated. The following results were obtained:

| SUPPORT | PARSOL MCX CONTENT | SIZE OF MICRO-CAPSULE | UVB PROTECTION INDEX |
| --- | --- | --- | --- |
| EMULSIONS | | | |
| Ex 3 | 5.28 | 100–125 | 5.16 |
| Ex 4 | 7.92 | | 6.95 |
| | 6.6 | no microcapsule | 4.37 |
| OILY GEL | | | |
| Ex 5 | 7.6 | 100–125 | 10.3 |
| | 7.6 | no microcapsule | 9.3 |

These results show that the protection index of sun filters placed inside impervious microcapusles of the invention was higher than that of non-encapsulated sun filters.

Various modifications of the products and method of the invention may be made without departing from the spirit or scope thereof, and it is to be understood that the invention is intended to be limited only as defined in the appended claims.

What is claimed is:

1. Microcapsules containing at least one sun filter having been hardened so as to be impervious with a size of 30 to 80 micrometers.

2. Microcapsules of claim 1 wherein the wall of the microcapsules contain gelatin which has been hardened.

3. Microcapsules of claim 2 wherein the gelatin has been hardened with glutaraldehyde.

4. Microcapsules of claim 1 with a size of 40 to 45 micrometers.

5. Microcapsules of claim 1 wherein the sun filters are selected from the group consisting of octyl methoxycinnamate, hexyl ethyl 4-methoxycinnamate, camphorous methylbenzylidene, isoamyl methoxycinnamate, octydimethyl PABA, PABA, homosalate, octyl salicylate, butyl methoxydibenzoylmethane, isopropyl dibenzoylmethane, oxybenzone and octyl triazone.

6. Microcapsules of claim 5 wherein the sun filters are diluted in an oil.

7. A cosmetic composition containing microcapsules of claim 1.

8. A pharmaceutical composition containing microcapsules of claim 1.

9. In a cosmetic treatment in which a cosmetic composition is applied to the skin, the improvement comprising using the composition of claim 7.

10. A process for the preparation of microcapsules of claim 1 comprising forming a dispersion of the sun filter in a colloidal solution, subjecting the dispersion to coacervation and formation of a ternary system by pH variation, encapsulating the dispersed sun filter, hardening the walls of the microcapsules and recovery of the microcapsules.

11. An antisun composition comprising an antisolar effective amount of microcapsules with a size of 30 to 80 micrometers containing at least one sun filter, the capsules having walls containing gelatin having been hardened so as to be impervious so that the sun filters will not leak out during storage or use.

12. An anti-sun composition comprising an anti-solar effective amount of microcapsules having a size of 20 to 200 micrometers containing at least one sun filter, the capsules having walls containing gelatin having been hardened with glutaraldehyde whereby the capsules are impervious and the sun filters cannot leak out during storage or use.

13. Microcapsules containing a sun filter selected from the group consisting of octyl methoxycinnamate and butyl methoxydibenzoylmethane having been hardened with glutaraldehyde so as to be impervious with a size of 30 to 80 micrometers.

* * * * *